US011523480B2

(12) United States Patent
Lamoureux (10) Patent No.: US 11,523,480 B2
(45) Date of Patent: Dec. 6, 2022

(54) METHOD AND SYSTEM FOR CALIBRATION OF UV LIGHT SOURCES (71) Applicant: Phoseon Technology, Inc., Hillsboro, OR (US)

(72) Inventor: Tegan Lamoureux, Portland, OR (US)

(73) Assignee: Phoseon Technology, Inc., Portland, OR (US)

( * ) Notice: Subject to any disclaimer, the term of this patent is extended or adjusted under 35 U.S.C. 154(b) by 66 days.

(21) Appl. No.: 16/424,336

(22) Filed: May 28, 2019

(65) Prior Publication Data

US 2019/0365937 A1 Dec. 5, 2019

Related U.S. Application Data (60) Provisional application No. 62/678,769, filed on May 31, 2018.

(51) Int. Cl.
*G01J 1/44* (2006.01)
*H05B 45/18* (2020.01)
*A61L 2/10* (2006.01)
*A61L 2/24* (2006.01)
*H05B 45/12* (2020.01)

(52) U.S. Cl.
CPC ............... *H05B 45/18* (2020.01); *A61L 2/10* (2013.01); *A61L 2/24* (2013.01); *A61L 2202/11* (2013.01); *A61L 2202/14* (2013.01); *G01J 2001/444* (2013.01); *H05B 45/12* (2020.01)

(58) Field of Classification Search
CPC .......... A61L 2/10; A61L 2/24; A61L 2202/11; A61L 2202/14; A61L 2202/23; H05B 45/10; H05B 45/12; H05B 45/18; G01J 2001/444
See application file for complete search history.

(56) References Cited

U.S. PATENT DOCUMENTS

| 8,222,574 | B2* | 7/2012 | Sorabji | H01L 21/67115 |
| | | | | 219/444.1 |
| 8,426,800 | B2 | 4/2013 | Ingram et al. | |
| 9,024,535 | B2* | 5/2015 | Picciotto | H05B 45/12 |
| | | | | 250/238 |
| 10,378,748 | B2* | 8/2019 | Ott | H05B 45/24 |
| 2005/0230600 | A1 | 10/2005 | Olson et al. | |
| 2010/0277410 | A1 | 11/2010 | You et al. | |
| 2011/0073838 | A1* | 3/2011 | Khan | H01L 27/153 |
| | | | | 257/13 |

(Continued)

FOREIGN PATENT DOCUMENTS

KR 20180053661 A 5/2018

OTHER PUBLICATIONS

ISA Korean Intellectual Property Office, International Search Report and Written Opinion Issued in Application No. PCT/US2019/034217, dated Sep. 20, 2019, WIPO, 13 pages.

*Primary Examiner* — Christine S. Kim
(74) *Attorney, Agent, or Firm* — McCoy Russell LLP (57) ABSTRACT

Methods and systems are provided for calibrating a UV lamp having a plurality of arrays or channels of light emitting diodes. The calibration involves adjusting a drive current applied to the UV lamp based on an actual irradiance output by its light-emitting diodes relative to a target irradiance. The calibration is selectively performed when a stabilized temperature condition of the lamp is met.

20 Claims, 5 Drawing Sheets

(56) References Cited

U.S. PATENT DOCUMENTS

| | | | |
|---|---|---|---|
| 2011/0121749 A1* | 5/2011 | Kubis | H05B 45/50 |
| | | | 315/291 |
| 2015/0083933 A1* | 3/2015 | Eliason | H01L 33/06 |
| | | | 250/459.1 |
| 2016/0212827 A1* | 7/2016 | Johnson, III | H05B 45/14 |
| 2016/0287897 A1 | 10/2016 | Kaestle | |
| 2018/0045666 A1* | 2/2018 | Sims | G01N 27/286 |
| 2018/0138161 A1 | 5/2018 | Spiegler et al. | |
| 2020/0149706 A1* | 5/2020 | Khosla | F21V 7/043 |

* cited by examiner

METHOD AND SYSTEM FOR CALIBRATION OF UV LIGHT SOURCES

CROSS REFERENCE TO RELATED APPLICATIONS

The present application claims priority to U.S. Provisional Application No. 62/678,769, entitled "METHOD AND SYSTEM FOR CALIBRATION OF UV LIGHT SOURCES", and filed on May 31, 2018. The entire contents of the above-listed application are hereby incorporated by reference for all purposes.

FIELD

The present description relates generally to methods and systems for concurrently calibrating a plurality of UV light sources.

BACKGROUND/SUMMARY

Solid-state lighting devices have many uses in industrial applications. For example, ultraviolet (UV) lighting devices have become fairly common for curing photo sensitive media such as coatings, including inks, adhesives, preservatives, etc. Curing time of these photo sensitive media may be controlled via adjusting intensity of light directed at the photo sensitive media or the amount of time that the photo sensitive media is exposed to light from the solid-state lighting device. As another example, UV lighting devices may be used in ultraviolet germicidal irradiation (UVGI), a disinfection method that uses short-wavelength ultraviolet (UV-C and/or UV-B) light to kill or inactivate microorganisms and enzymes (e.g., RNase). UVGI is extensively used for decontaminating laboratory equipment and reagents, including microplates. Overall, solid-state lighting devices typically use less power, cost less, and may have easier disposal than current mercury arc lamp devices.

Solid-state lighting devices may consist of laser diodes or light-emitting diodes (LEDs) as examples. The device typically has an array or several arrays arranged to provide light with a particular profile, such as a long, thin light region, or wider and deeper light regions. The individual elements reside in arrays or parallel and/or series connected emitters to form an individual semiconductor light matrix (or SLM). A lighting device may comprise several arrays, or several arrays arranged in modules, with the lighting device having several modules.

Such solid-state lighting devices, also referred to as a semiconductor light matrix (SLM) lamp, may be operated to provide ultraviolet (UV) light for curing photosensitive adhesives and media or decontaminating laboratory equipment and reagents. Typically, such lamps require output equalization across SLM channels and calibration to a target irradiance before the lamp is usable, as the individual diode characteristics result in varying drive currents being required to achieve a given output intensity. These two processes are mutually inclusive. That is, in order to have a known target irradiance under the entire area of illumination by the lamp, the irradiance of all channels must be within a given output percentage of each other. As an example, if the SLM channels are not calibrated prior to use in curing photosensitive adhesives and media, the target irradiance may not be achieved across the irradiated media, resulting in uneven and/or incomplete curing. As another example, if the SLM channels are not calibrated prior to use in UVGI, the target irradiance may not be achieved across the irradiated laboratory equipment, resulting in incomplete decontamination.

Existing methods of equalizing output across a multi-channel lamp involve manually adjusting the drive current of individual SLM channels over a fixed meter external to the final appliance. However, there are various potential issues with such an approach. The issues may include human error, reduced repeatability of temperature and environmental factors, and the potential for operator exposure to dangerous wavelengths of UV light. The manual adjustment may involve modifying either a digital or a mechanical potentiometer controlling the drive current of the SLM channel. In the case of a mechanical potentiometer, the adjustment requires physical access to the driver circuit board and lamp, and involves fine-tuning a component on the circuit board to control drive current while observing output from a fixed external irradiance meter. In the case of a digital potentiometer, the adjustment requires using a controlling computer connected to the lamp to change drive current by numeric entry into a program field while observing output from a fixed external irradiance meter.

Both adjustment methods can introduce potential error into the process, as all adjustments and the irradiance readings these adjustments rely on are performed and observed by a human operator. Alongside this, the irradiance of the SLM UV diodes is a function of temperature, which increases with time to an eventual equilibrium. Any output balancing or calibration cannot proceed until this equilibrium point is reached. The determination of when this equilibrium is reached also relies on operator observance. These methods can also introduce the potential for operator exposure to wavelengths of ultraviolet radiation, as they must physically move the lamp to index the individual channel over the fixed irradiance meter.

Furthermore, UVC wavelength diodes are in their infancy, having just come out of research and development. As a result, they have a highly variable and greater lifetime intensity decay factor than higher wavelength UV diodes. As a result, higher wavelength diodes typically are stable over the product lifetime, and only require balance and target calibration once during the manufacturing process. This is in contrast to UVC diodes, which necessitate multiple rebalance and target output calibration procedures over their lifetime in order to maintain a homogenous output across the entire illumination area at the target irradiance. Because of the variability of decay and drive current requirements, individual SLM channels may require different amounts of current increases over their lifetime to keep the entire array balanced.

The inventors herein have recognized the above-mentioned issues and have engineered a way to at least partially address them. One example approach for improving UV lamp calibration includes utilizing, via an algorithm run on a controller, narrow-band UVC photodiodes to both equalize output across a multi-channel Semiconductor Light Matrix (SLM) lamp, and calibrate the lamp to a target output irradiance. Additionally, temperature regression analysis can be used via the algorithm in conjunction with a digital thermocouple to accurately determine thermal equilibrium across a wide range of operational environmental conditions. This enables the increased output decay factor of the diodes to be leveraged in seeing an increasing equilibrium temperature, along with a changing time-to-equilibrium over the lighting system's service life.

The present description may provide several advantages. In particular, the approach may improve lighting system calibration by enabling the lighting system to be calibrated across a wide range of operational conditions. Further, the lighting system may be calibrated and equalized across the product's life cycle without exposing an operator to UV radiation. By reducing the requirement for a technician to gain access or intervene, the human error contribution to the calibration routine may be significantly reduced.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
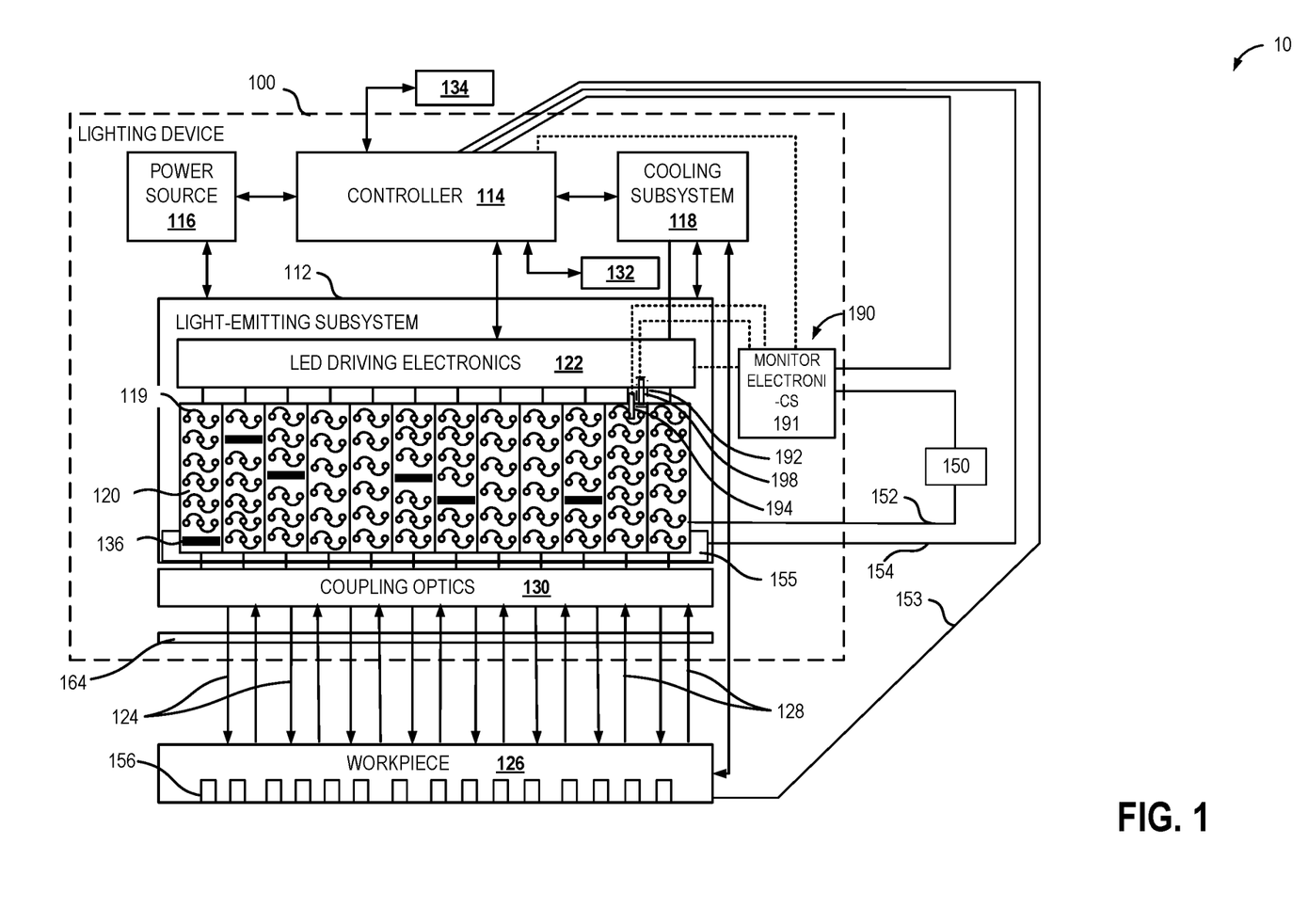
FIG. 1 shows a schematic depiction of a semiconductor lighting system.
Figure 4:
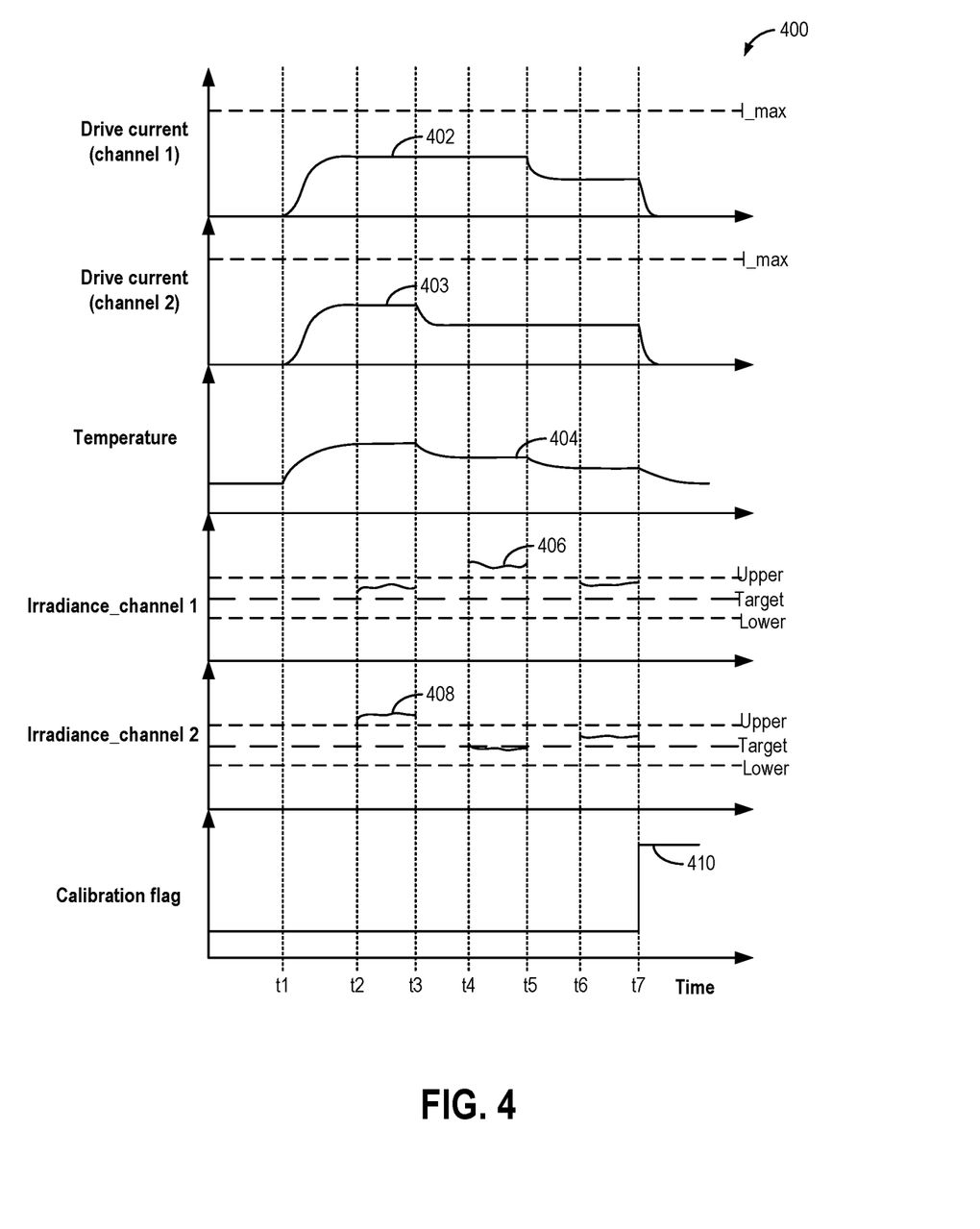
FIG. 4 shows a prophetic timeline of calibration of a solid-state UV lamp.
Figure 5:
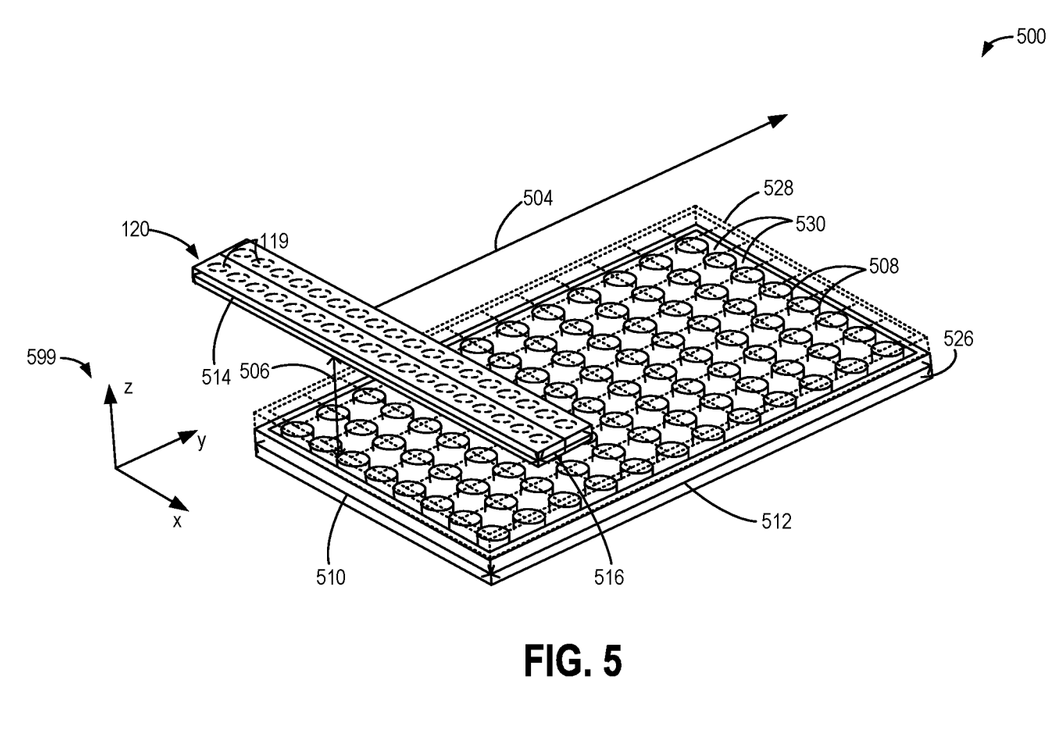
FIG. 5 shows an example array of a semiconductor lighting system positioned over an array of lenses covering a microplate.

The present description is related to a semiconductor lighting system, such as the lighting system of FIG. 1. The lighting system may be operated according to the method of FIG. 2 to enable each of the light arrays of the lighting system to be equalized with one another and calibrated. During the calibration, a drive current directed to the solid-state lighting system may be adjusted via a circuit, such as the circuit of FIG. 3. A prophetic example of semiconductor lighting system calibration is shown at FIG. 4. Once calibrated, the semiconductor lighting system may be used to decontaminate a microplate, such as shown in FIG. 5.

Referring now to FIG. 1, it illustrates a block diagram for an example configuration of a lighting device 100 that may be included in an irradiation system 10. In one example, lighting device 100 may comprise a light-emitting subsystem 112, a controller 114, a power source 116 and a cooling subsystem 118. The light-emitting subsystem 112 may comprise a plurality of semiconductor devices 119. In one example, where the plurality of semiconductor devices are arranged as a matrix, the light-emitting subsystem 112 may also be referred to as a semiconductor light matrix (SLM). The plurality of semiconductor devices 119 may include a linear or two-dimensional array 120 of light-emitting elements such as an array of LED devices, for example. In one example, the linear array 120 of light-emitting elements may create a semiconductor light matrix (SLM) channel. Semiconductor devices may provide radiant output 124, including one or more of visible light, ultra-violet (UV) light, and infrared (IR) radiation. The radiant output 124 may be directed to a workpiece 126 located at a fixed plane from lighting device 100. Returned radiation 128 may be retro-reflected back to the light-emitting subsystem 112 from the workpiece 126 (e.g., via reflection of the radiant output 124). In some examples, the workpiece 126 may include a retro-reflective surface.

Power source 116 may be configured to provide a drive current to light emitting subsystem 112 so as to generate the radiant output 124. In one example, power source 116 is a battery.

The radiant output 124 may be directed to the workpiece 126 via coupling optics 130. The coupling optics 130, if used, may be variously implemented. As an example, the coupling optics may include one or more layers, materials, or other structures interposed between the semiconductor devices 119 and workpiece 126, and providing radiant output 124 to surfaces of the workpiece 126. As an example, the coupling optics 130 may include a micro-lens array to enhance collection, condensing, collimation or otherwise the quality or effective quantity of the radiant output 124. As another example, the coupling optics 130 may include a micro-reflector array. In employing such a micro-reflector array, each semiconductor device providing radiant output 124 may be disposed in a respective micro-reflector, on a one-to-one basis. As another example, a linear array of semiconductor devices 120 providing radiant output 124 may be disposed in macro-reflectors, on a many-to-one basis. In this manner, coupling optics 130 may include both micro-reflector arrays, wherein each semiconductor device is disposed on a one-to-one basis in a respective micro-reflector, and macro-reflectors wherein the quantity and/or quality of the radiant output 124 from the semiconductor devices is further enhanced by macro-reflectors. Lighting device 100 may further include a transparent window 164 (or chamber glass) interposed between the coupling optics 130 and the workpiece 126.

Each of the layers, materials or other structure of coupling optics 130 may have a selected index of refraction. By properly selecting each index of refraction, reflection at interfaces between layers, materials and other structures in the path of the radiant output 124 (and/or retro-reflected radiation 128) may be selectively controlled. As an example, by controlling differences in such indexes of refraction at a selected interface, for example window 164, disposed between the semiconductor devices to the workpiece 126, reflection at that interface may be reduced or increased so as to enhance the transmission of radiant output at that interface for ultimate delivery to the workpiece 126. For example, the coupling optics may include a dichroic reflector where certain wavelengths of incident light are absorbed, while others are reflected and focused to the surface of workpiece 126.

The coupling optics 130 may be employed for various purposes. Example purposes include, among others, to protect the semiconductor devices 119, to retain cooling fluid associated with the cooling subsystem 118, to collect, condense and/or collimate the radiant output 124, to collect, direct or reject retro-reflected radiation 128, or for other purposes, alone or in combination. As a further example, the lighting device 100 may employ coupling optics 130 so as to enhance the effective quality, uniformity, or quantity of the radiant output 124, particularly as delivered to the workpiece 126.

As a further example, coupling optics 130 may comprise a cylindrical lens through which light emitted from the linear array of light-emitting elements is directed. As previously described, light emitted from the linear array of light-emitting elements may be incident at an incident face of the cylindrical lens, and may be collimated and redirected out of an emitting face of the cylindrical lens. The cylindrical lens may include one or more of a rod lens, a semi-circular lens, a plano-convex lens, a bi-convex lens, and a faceted Fresnel lens. The cylindrical lens may include a cylindrical lens having a cylindrical power axis and an orthogonal plano-axis, for collimating and/or focusing the light emitted from the linear array 120 of semiconductor devices 119.

Selected of the plurality of semiconductor devices 119 may be coupled to the controller 114 via LED driving electronics 122, so as to provide data to the controller 114. As described further below, the controller 114 may also be implemented to control such data-providing semiconductor devices, e.g., via the LED driving electronics 122. The controller 114 may be connected to, and may be implemented to control, the power source 116, and the cooling subsystem 118. Moreover, the controller 114 may receive data from power source 116 and cooling subsystem 118. In one example, the irradiance at one or more locations at the workpiece 126 surface may be detected by sensors and transmitted to controller 114 in a feedback control scheme. In a further example, controller 114 may communicate with a controller of another lighting system (not shown in FIG. 1) to coordinate control of both lighting systems. For example, controller 114 of multiple lighting systems may operate in a master-slave cascading control algorithm, where the set point of one of the controllers is set by the output of the other controller. Other control strategies for operation of lighting device 100 in conjunction with another lighting system may also be used. As another example, controller 114 for multiple lighting systems arranged side by side may control lighting systems in an identical manner for increasing uniformity of irradiated light across multiple lighting systems. As yet another example, controller 114 may adjust a drive current applied to the light-emitting subsystem 112 based on feedback regarding the radiant output 124 (e.g., based on whether the irradiance is at or within a threshold of a target value).

In addition to the power source 116, cooling subsystem 118, and light-emitting subsystem 112, the controller 114 may also be connected to, and implemented to control internal element 132, and external element 134. Element 132, as shown, may be internal to the lighting device 100, while element 134, as shown, may be external to the lighting device 100, but may be associated with the workpiece 126 (e.g., handling, cooling or other external equipment) or may be otherwise related to a photoreaction (e.g. curing) that lighting device 100 supports.

The data received by the controller 114 from one or more of the power source 116, the cooling subsystem 118, the light-emitting subsystem 112, and/or elements 132 and 134, may be of various types. As an example, the data may be representative of one or more characteristics associated with coupled semiconductor devices 119. As another example, the data may be representative of one or more characteristics associated with the respective light-emitting subsystem 112, power source 116, cooling subsystem 118, internal element 132, and external element 134 providing the data. As still another example, the data may be representative of one or more characteristics associated with the workpiece 126 (e.g., representative of the radiant output energy or spectral component(s) directed to the workpiece). Moreover, the data may be representative of some combination of these characteristics.

The controller 114, in receipt of any such data, may be implemented to respond to that data. For example, responsive to such data from any such component, the controller 114 may be implemented to control one or more of the power source 116, cooling subsystem 118, light-emitting subsystem 112 (including one or more such coupled semiconductor devices), and/or the elements 132 and 134. As an example, responsive to data from the light-emitting subsystem indicating that the light energy is insufficient at one or more points associated with the workpiece, the controller 114 may be implemented to either (a) increase the power source's supply of power (e.g., drive current or voltage) to one or more of the semiconductor devices, (b) increase cooling of the light-emitting subsystem via the cooling subsystem 118 (e.g., certain light-emitting devices, if cooled, provide greater radiant output), (c) increase the time during which the power is supplied to such devices, or (d) a combination of the above.

Individual semiconductor devices 119 (e.g., LED devices) of the light-emitting subsystem 112 may be controlled independently by controller 114. For example, controller 114 may control a first group of one or more individual LED devices to emit light of a first intensity, wavelength, and the like, while controlling a second group of one or more individual LED devices to emit light of a different intensity, wavelength, and the like. The first group of one or more individual LED devices may be within the same linear array 120 of semiconductor devices, or may be from more than one linear array of semiconductor devices 120 from multiple lighting devices 100. Linear array 120 of semiconductor device may also be controlled independently by controller 114 from other linear arrays of semiconductor devices in other lighting systems. For example, the semiconductor devices of a first linear array may be controlled to emit light of a first intensity, wavelength, and the like, while those of a second linear array in another lighting system may be controlled to emit light of a second intensity, wavelength, and the like.

As a further example, under a first set of conditions (e.g. for a specific work piece, photoreaction, and/or set of operating conditions) controller 114 may operate irradiation system 10 to implement a first control strategy, whereas under a second set of conditions (e.g. for a specific work piece, photoreaction, and/or set of operating conditions) controller 114 may operate irradiation system 10 to implement a second control strategy. As described above, the first control strategy may include operating a first group (e.g., a first sub lighting array) of one or more individual semiconductor devices (e.g., LED devices) to emit light of a first intensity, wavelength, and the like, while the second control strategy may include operating a second group (e.g., a second sub lighting array) of one or more individual LED devices to emit light of a second intensity, wavelength, and the like. The first group of LED devices may be the same group of LED devices as the second group, and may span one or more arrays of LED devices, or may be a different group of LED devices from the second group, and the different group of LED devices may include a subset of one or more LED devices from the second group.

The cooling subsystem 118 may be implemented to manage the thermal behavior of the light-emitting subsystem 112. For example, the cooling subsystem 118 may provide for cooling of light-emitting subsystem 112, and more specifically, the semiconductor devices 119. The cooling subsystem 118 may also be implemented to cool the workpiece 126 and/or the space between the workpiece 126 and the lighting device 100 (e.g., the light-emitting subsystem 112). For example, cooling subsystem 118 may comprise an air or other fluid (e.g., water) cooling system. Cooling subsystem 118 may also include cooling elements such as cooling fins attached to the semiconductor devices 119, or linear array 120 thereof, or to the coupling optics 130. For example, cooling subsystem may include blowing cooling air over the coupling optics 130, wherein the coupling optics 130 are equipped with external fins to enhance heat transfer.

The lighting device 100 may be used for various applications. Examples include, without limitation, curing applications ranging from displays, photoactive adhesives, and ink printing to the fabrication of DVDs and lithography, as well as decontamination applications (e.g., ultraviolet germicidal irradiation). The applications in which the lighting device 100 may be employed can have associated operating parameters. That is, an application may have associated operating parameters as follows: provision of one or more levels of radiant power, at one or more wavelengths, applied over one or more periods of time. In order to properly accomplish the photoreaction or decontamination associated with the application, optical power may be delivered at or near the workpiece 126 at or above one or more predetermined levels of one or a plurality of these parameters (and/or for a certain time, times or range of times).

In order to follow an intended application's parameters, the semiconductor devices 119 providing radiant output 124 may be operated in accordance with various characteristics associated with the application's parameters, e.g., temperature, spectral distribution and radiant power. At the same time, the semiconductor devices 119 may have certain operating specifications, which may be associated with the semiconductor devices' fabrication and, among other things, may be followed in order to preclude destruction and/or forestall degradation of the devices. Other components of the lighting device 100 may also have associated operating specifications. These specifications may include ranges (e.g., maximum and minimum) for operating temperatures and applied electrical power, among other parameter specifications.

Accordingly, the lighting device 100 may support monitoring of the application's parameters. In addition, the lighting device 100 may provide for monitoring of semiconductor devices 119, including their respective characteristics and specifications. Moreover, the lighting device 100 may also provide for monitoring of selected other components of the lighting device 100, including its characteristics and specifications.

Providing such monitoring may enable verification of the system's proper operation so that operation of lighting device 100 may be reliably evaluated. For example, lighting device 100 may be operating improperly with respect to one or more of the application's parameters (e.g. temperature, spectral distribution, radiant power, and the like), any component's characteristics associated with such parameters, and/or any component's respective operating specifications. The provision of monitoring may be responsive to and carried out in accordance with the data received by the controller 114 from one or more of the system's components.

Monitoring may also support control of the system's operation. For example, a control strategy may be implemented via the controller 114, the controller 114 receiving and being responsive to data from one or more system components. This control strategy, as described above, may be implemented directly (e.g., by controlling a component through control signals directed to the component, based on data respecting that components operation) or indirectly (e.g., by controlling a component's operation through control signals directed to adjust operation of other components). As an example, a semiconductor device's radiant output may be adjusted indirectly through control signals directed to the power source 116 that adjust power applied to the light-emitting subsystem 112 and/or through control signals directed to the cooling subsystem 118 that adjust cooling applied to the light-emitting subsystem 112.

Control strategies may be employed to enable and/or enhance the system's proper operation and/or performance of the application. In one example, the irradiance at one or more locations at the workpiece 126 surface may be detected by photosensors and transmitted to controller 114 in a feedback control scheme, such as a calibration scheme described with respect to FIG. 2.

In some applications, high radiant power may be delivered to the workpiece 126. Accordingly, the light-emitting subsystem 112 may be implemented using an array of light-emitting semiconductor devices 120. For example, the light-emitting subsystem 112 may be implemented using a high-density light-emitting diode (LED) array. Although linear arrays of light-emitting elements may be used and are described in detail herein, it is understood that the semiconductor devices 119, and linear arrays 120 thereof, may be implemented using other light-emitting technologies without departing from the principles of the invention. Examples of other light-emitting technologies include, without limitation, organic LEDs, laser diodes, and other semiconductor lasers.

Continuing with FIG. 1, the plurality of semiconductor devices 119 may be provided in the form of one or more arrays 120, or an array of arrays (e.g., as shown in FIG. 1). The arrays 120 may be implemented so that one or more or most of the semiconductor devices 119 are configured to provide radiant output. At the same time, however, one or more of the array's semiconductor devices 119 may be implemented so as to provide for monitoring selected of the array's characteristics. One or more monitoring devices 136 may be selected from among the devices in the array and, for example, may have the same structure as the other, emitting semiconductor devices. For example, the difference between emitting and monitoring may be determined by the LED driving electronics 122 associated with the particular semiconductor device (e.g., in a basic form, an LED array may have monitoring LED devices where the coupling electronics provide a reverse current, and emitting LED devices where the coupling electronics provide a forward current).

Furthermore, based on coupling electronics, selected of the semiconductor devices in the array may be either/both multifunction devices and/or multimode devices, where (a) multifunction devices may be capable of detecting more than one characteristic (e.g., either radiant output, temperature, magnetic fields, vibration, pressure, acceleration, and other mechanical forces or deformations) and may be switched among these detection functions in accordance with the application parameters or other determinative factors and (b) multimode devices may be capable of emission, detection and some other mode (e.g., off) and may be switched among modes in accordance with the application parameters or other determinative factors.

A radiation monitor 190, or radiation monitoring device, for monitoring radiation output by the lighting device 100 may include a first sensor 194, a second sensor 198 and monitor electronics 191. In one example, the radiation monitor is a potentiometer. Furthermore, the radiation monitor 190 may include a radiation filter 192. In one example, the radiation filter 192 may comprise a device or structure coupled to the second sensor 198. In one example, the radiation filter 192 may be coupled directly to the second sensor; in other examples, the radiation filter 192 may be coupled indirectly with the second sensor. In other examples, the radiation filter may include a structure separate from the second sensor that, when taken in conjunction with positioning of the second sensor, serves as a spatial radiation filter to exclude the radiation output directly from the lighting device from reaching the second sensor while allowing radiation output from external sources to be received at the second sensor. In other words, the radiation filter 192 may shield the second sensor 198 from the radiation output directly by the light-emitting element while allowing the radiation from external sources to reach the second sensor, while the radiation output directly from the light-emitting element and the radiation from external sources are incident at the first sensor 194.

Monitor electronics 191 may be coupled to the light emitting system via a temperature sensor 150. In one example, a device or structure 152 may couple the monitor electronics 191 to the temperature sensor 150.

Examples of the radiation filter 192 may include a mounting means for positioning the second and/or first sensors, and light capillaries. Furthermore, shielding the second sensor 198 from the radiation output directly from the light-emitting element while allowing the radiation from external sources to reach the second sensor may be implemented by one or more of positioning the second sensor 198 at a non-light-emitting side of a light-emitting plane of the light-emitting element 119, supporting the light-emitting element 119 on a base interposed between a printed circuit board of the lighting device 100 and the light-emitting element 119 to facilitate positioning the second sensor 198 at the non-light emitting side of the light-emitting plane of the light-emitting element 119, and coupling a light capillary to the second sensor 198.

The first sensor 194 and the second sensor 198 may include thermocouples. In another example, the first sensor 194 and the second sensor 198 may include photodiodes. In other examples, first sensor 194 and the second sensor 198 may include another type of photosensor or radiation sensor. The radiation monitor 190 may be a standalone device (as shown at the bottom of FIG. 1), and may be retrofit to existing lighting devices for monitoring the power (or radiation intensity) output therefrom. Retrofitting the radiation monitor 190 with a lighting device 100 may include positioning the first sensor 194 and second sensor 198 adjacent to a light-emitting element of the lighting device 100. Additionally, the radiation monitor 190 may be more closely integrated (as shown in FIG. 1) with a lighting device by conductively coupling the monitor electronics 191 with LED driving electronics 122 and/or controller 114 of the lighting device. In this way, the lighting device operation may be modulated or controlled responsively to measurements from the radiation monitor 190, including responsively to signals from the first and second sensors 194 and 198 and monitor electronics 191.

For example, if the radiation monitor 190 detects a radiation output directly from the lighting device that is greater than a threshold radiation output, the controller 114 may send a signal to the LED driving electronics 122 of the lighting device 100 to reduce a power output from the array 120 of light-emitting elements 119. As another example, if the radiation monitor 190 detects a radiation output directly from the lighting device that is less than a threshold radiation output, the controller 114 may send a signal to the LED driving electronics 122 of the lighting device 100 to increase a power output from the array 120 of light-emitting elements 119. More accurate and reliable measurement of the radiation output directly from the lighting device 100 with the radiation monitor 190 may be further incorporated to increase an accuracy and reliability of existing control strategies and algorithms of the lighting device 100, as described above. In this way, discrepancies between the radiation output of the lighting device 100 and a threshold or target radiation output from the lighting device 100 may be reduced.

For example, the controller 114 may adjust power source 116 and/or cooling subsystem 118 in response to data received from monitor electronics 191. In one example, a lower than threshold radiation output measured by the radiation monitor 190 for a given power input from power source 116 may indicate that the lighting device 100 may be overheated. In this case, the controller 114 may adjust cooling subsystem 118 to increase a cooling capacity delivered to the light-emitting subsystem 112 to reduce a temperature threat. In a further example, multiple lighting devices 100 may each include integrated radiation monitors 190 for measuring the radiation output therefrom and for coordinating control of both lighting systems in parallel. For example, controller 114 of multiple lighting systems may operate in a master-slave cascading control algorithm, where the set point of one of the controllers is set by the output of the other controller. Other control strategies for operation of lighting device 100 in conjunction with another lighting system may also be used. In another representation, controller 114 for multiple lighting systems arranged side by side may control lighting systems in an identical manner for increasing uniformity of irradiated light across multiple lighting systems. In one embodiment, one set of monitor electronics 191 may be coupled to multiple pairs of first and second sensors 194 and 198 for communicating with and measuring radiation output from multiple lighting devices 100. In this way, a controller 114 for multiple lighting devices may communicate with a single monitoring electronics 191 for controlling the multiple lighting devices 100, thereby simplifying controller wiring and programming.

The channels or arrays 120 of the SLM may be positioned relative to UV photosensors 156 (e.g., photointerrupter sensors) via a motorized linear stage 155 based on control signals 154 received at the linear stage from controller 114. The photosensors 156 may be photodiodes, for example, and may transmit an output signal 153 to controller 114 corresponding to a detected amount of irradiance. The linear stage may include a motor, such as a stepper motor, to adjust the position of the SLM, optics, etc. As an example, the photosensors 156 may be positioned at a specific location on the surface of workpiece 126, and a position of the channels or arrays 120 of the SLM may be adjusted along a single, horizontal axis (e.g., perpendicular to a direction of the radiant output 124) by the motorized linear stage 155 so that the SLM is centered above the photosensors 156 instead of a target area of irradiance of the workpiece 126 that is used for photoreactions and/or decontamination. In one example, as elaborated with reference to FIG. 2, during lamp calibration and channel equalization, the photosensors are centered under the above placed channels when the SLM unit is "homed". The home position may be sensed by one or more sensors. In an alternative example, the position of the SLM may be static, and the position of the photosensors 156 may be adjusted by a similar linear stage so that the photosensors 156 are centered under the channels or arrays 120 of the SLM. In a further example, responsive to the control signals 154, the motorized linear stage 155 may move the array 120 along the single, horizontal axis in order to target irradiance to different areas of a microplate, as further described below with respect to FIG. 5.

The inventors herein have recognized that an accurate irradiance reading from the light emitting system and therein included SLM UVC diodes may not be made until the lighting device has reached a thermal equilibrium. This is because the output of individual semiconductor devices (e.g. diodes) can change dramatically with temperature fluctuations. The time to reach this temperature equilibrium is affected by multiple factors, from ambient operating conditions to diode characteristics and age. This may make it exceedingly difficult to characterize a given lighting device (herein also referred to as a lamp). In one example, as described with reference to FIG. 2, a linear regression analysis of the temperature over time may be used to determine when thermal equilibrium is reached.

One example implementation of the regression analysis leverages a thermocouple attached to the lamp's heat sink. With an attached thermocouple to the lamp's heat sink, to which the SLM channels and arrays are all mounted, a temperature reading can be made in firmware to determine an estimated diode operating temperature. As it may be difficult to monitor and track this temperature over time, a circular buffer may be used to keep track of the last n temperature readings. Given a buffer with n=120, and a measurement frequency of 0.5 seconds, the last minute of thermal behavior of the lamp may be stored. By performing a linear regression analysis of this circular buffer once every second, and monitoring the slope of this line, a characterization can be made for the rate of change in temperature (in Degrees Celsius per Second). By setting and checking for a fixed threshold rate of change, such as 0.25° C./second, the controller may accurately and reliably determine when a lamp is at sufficient equilibrium, regardless of the final equilibrium temperature, time to equilibrium, and ambient operating conditions.

Further improvements in correlating between a given UV diode power output (in $mW/cm^2$) and a photocurrent output from the diode (in nA) may be achieved via the use of AlGaN Schottky-Type Photodiodes sensitive to desirable UV wavelengths. Analog modification of the signal, fed into an Analog to Digital Converter (ADC), may enable the photocurrent output to be easily measured. As there may be some small variability in the reading, a series of multiple (e.g., five) measurements from the ADC may be taken at a frequency (e.g., of 200 ms) and averaged, giving a 1 second total time to acquire. This approach provides various advantages. For example, the photodiodes may be placed inside of the final appliance, which is adequately shielded from UV leakage, protecting the operator from UV exposure. Additionally, the equipment, means of acquiring the data, and analysis of the data, are all highly reliable, and no longer prone to human error.

Figure 2:
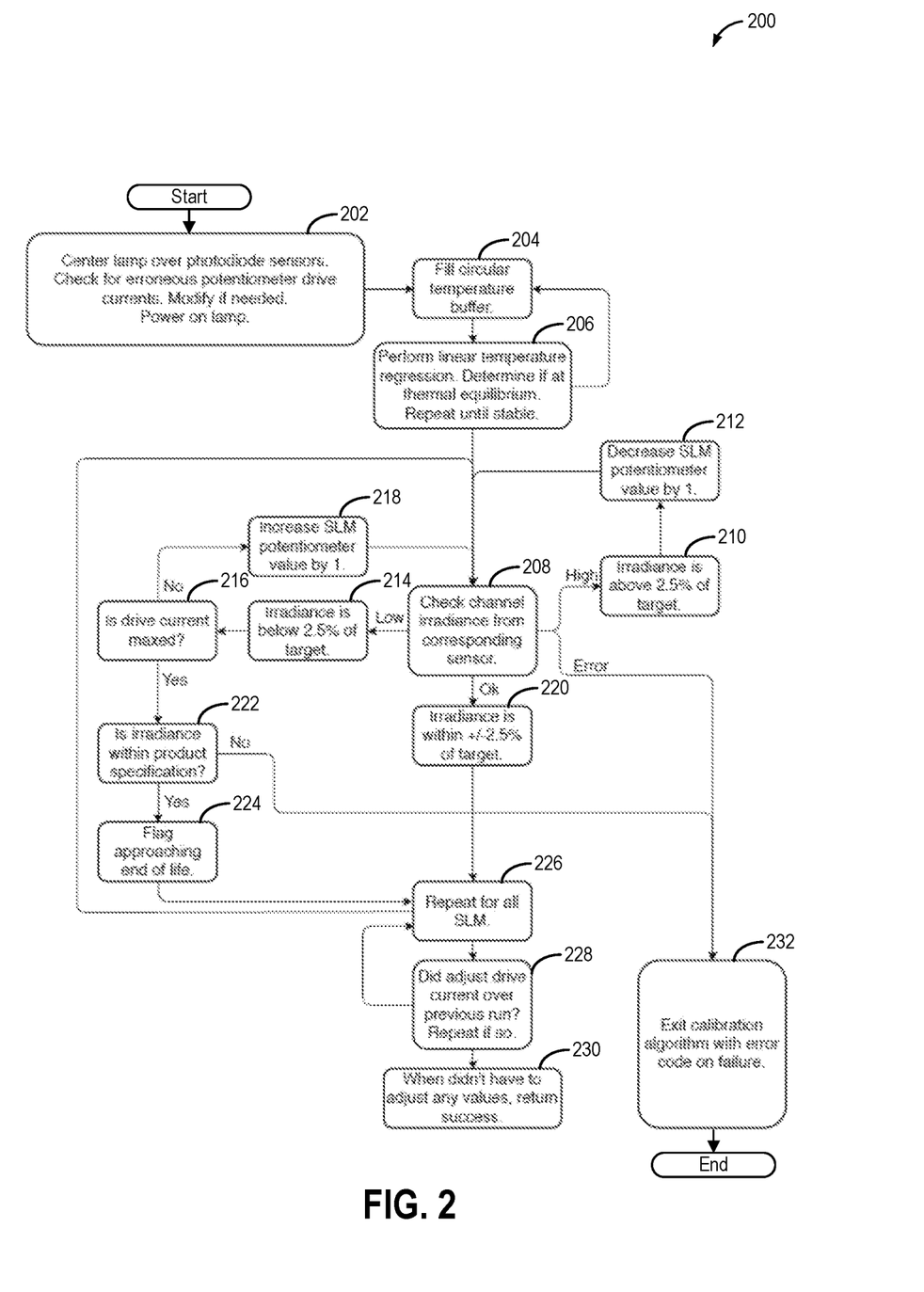
FIG. 2 shows a flowchart of a method for concurrently calibrating the lighting system of FIG. 1 and equalizing the diodes of the lighting system.

Turning now to FIG. 2, an example method 200 is shown for concurrent calibration and equalization of the plurality of semiconductor devices of an SLM array lighting device. In one example, the device is configured as a UV lamp. Instructions for carrying out method 200 and the rest of the methods included herein may be executed by a controller (e.g., controller 114 of FIG. 1) based on instructions stored on a memory of the controller and in conjunction with signals received from sensors of the lighting device, such as the sensors described above with reference to FIG. 1. The controller may employ components and actuators of the lighting system to adjust a radiation output, according to the methods described below. In one example, the method 200 is reiterated once every 24 hours with a timing of running the method scheduled by a lamp operator, for example. In some examples, the method 200 may be performed after a predetermined number of operating hours, during preselected time periods of system downtime, and/or during preselected factory conditions such as when temperature in the factory environment has been stable for a threshold time period.

At 202, the method includes centering the lamp over the photosensors. For example, the controller may send a control signal to a motorized linear stage that moves the lamp along a single axis. Using the motorized linear stage, the lamp is moved to the calibration zone in order to center the lamp and channels over the photosensors. By moving the lamp to the calibration zone, the lamp is automatically centered over the photosensors, as opposed to the target area of irradiance. In one example, the lamp is centered over a first channel to be calibrated.

Also at 202, the method includes checking for erroneous potentiometer drive currents and modifying the currents if needed. In one example, the digital potentiometers controlling drive current of the channels are checked for erroneous or low values, indicating a previous error or an absence of previous calibrations, such as on a new product. Given a non-viable value, the controller may set the default starting potentiometer value on all channels that may require it, corresponding to a median drive current from observed diode characteristics. The method further includes starting with initial conditions where there are correlated UV photosensors such that a given photocurrent corresponds to a known irradiance. For example, prior to beginning method 200, the photosensors may be correlated to a known output for a given irradiance as a part of a one-time process during manufacturing. Therefore, if the UV photosensors have not been correlated, the method 200 may abort at 202. If the UV photosensors have been correlated, the lamp is turned on, and the linear regression analysis begins.

At 204, the method includes filling a circular temperature buffer. As an example, every 500 ms, the controller's firmware may read the value of an analog to digital converter (ADC) to determine the current heat sink temperature. This value is then stored in a circular buffer.

At 206, the method includes performing a linear temperature regression. The controller then repeats this until it is determined that thermal equilibrium has been reached and the system is stable. As an example, after the circular buffer fills (e.g., time=1 minute), the controller runs an algorithm that begins to perform a linear regression on this buffer, once every second. These two actions may continue until the linear regression results in a slope, or temperature rate of change, of 0.25° C./second or less, indicating the lamp is now at thermal equilibrium. Alternatively, if an error in reading the ADC occurs, the lamp exceeds maximum operating temperature, or a 15 minute timeout expires, the algorithm exits with a failure code.

At 208, the method includes checking the channel irradiance from the corresponding sensor. Herein, the sensor is the sensor corresponding to the channel being calibrated. In particular, once thermal equilibrium is reached, the balance and calibration section of the routine begins. Therein, starting with the first channel of the lamp, a reading from the corresponding photosensor is made by checking the value on the ADC tied to that sensor. As the reading is slightly variable, multiple (e.g., five) readings are taken are intervals (e.g., one every 200 ms) to accurately characterize the output intensity. A calculation is then made to determine the percent difference between the intensity measured by the photosensor and the desired target irradiance. The method then checks for certain error conditions before continuing.

If the channel irradiance is low, such as when the irradiance is below 2.5% of the target (at 214), it is determined further if the drive current is maxed out at 216. If yes, at 222, it is further determined if the irradiance is within the original product specification. If yes, that is if the potentiometer value has resulted in a maximum drive current, but the product is still within the original product specification, at 224, a flag is set or recorded to notify the user that the lamp is approaching end of life, as there is no more headroom for increasing drive current to compensate for diode output drop. The method then continues to 226.

If the potentiometer value has resulted in a minimum or maximum drive current for the electrical system (at 216), and the difference is greater than a preset allowable output deviance from the target irradiance for the product (No at 222), then at 232, the method exits and returns failure, as the desired irradiance was unable to be achieved. Likewise, if there is an error in the channel output, such as when the output is outside the range of the sensor, then the method moves to 232 to exit the routine with an error code being set. At 232, it is indicated, via the error code for example, that the lamp cannot be calibrated at this time.

If the channel irradiance is high, such as when the difference of the current channel's output is greater than 2.5% from the target irradiance (at 210), the method moves to 212 where the channel's drive current is reduced by decrementing the digital potentiometer by a single tick. In other words, the SLM potentiometer is decreased by a value of 1. As a result, the execution of the algorithm is delayed by 1 second in order to allow the intensity at the new drive current to stabilize. Additionally, a flag is set to note that a change to the drive current was made. The method then returns to 208 to resume checking the channel irradiance.

If the channel irradiance is low, such as when the difference of the current channel's output is less than 2.5% from the target irradiance (at 214), and the drive current is not maxed out at 216, the method moves to 218 where the channel's drive current is increased by incrementing the digital potentiometer by a single tick. The algorithm then delays by 1 second in order to allow the intensity at the new drive current to stabilize. Additionally, a flag is set to note that a change to the drive current was made. The method then returns to 208 to resume checking the channel irradiance.

If the difference in channel output is within 2.5% in either direction of the target, such as at 220, then no modification of the drive current is made and the method continues directly to 226. Therein, once the first channel is corrected, the controller moves onto a second channel and performs steps 208 onwards to calibrate and equalize the second channel based on channel irradiance estimated via a corresponding sensor. This is repeated until all channels have been adjusted. Since a modification to one channel will result in changing values for neighboring channels due to thermal differences and overlapping areas of irradiance, at 228, the method 200 includes checking the previously mentioned flag to determine if any changes were made to the channels during the last run. If so, the routine is repeated to ensure the output is again re-centered. Typically, three to five cycles of this section of the algorithm are seen. In this way, the routine is reiterated multiple times until the irradiance of each channel is within 2.5% of the target. Once a balancing has been completed and no changes were made, as determined at 228, and no errors in measurement or drive current were recorded, at 230, the method includes powering off the lamp and exiting the algorithm with a success code indicating successful completion of lamp calibration and channel equalization.

In this way, each section or channel of the solid-state UV-C lamp is tuned to other sections automatically and without operator input. By enabling the lamp to be automatically calibrated a balanced, lamp performance and life is improved.

Figure 3:
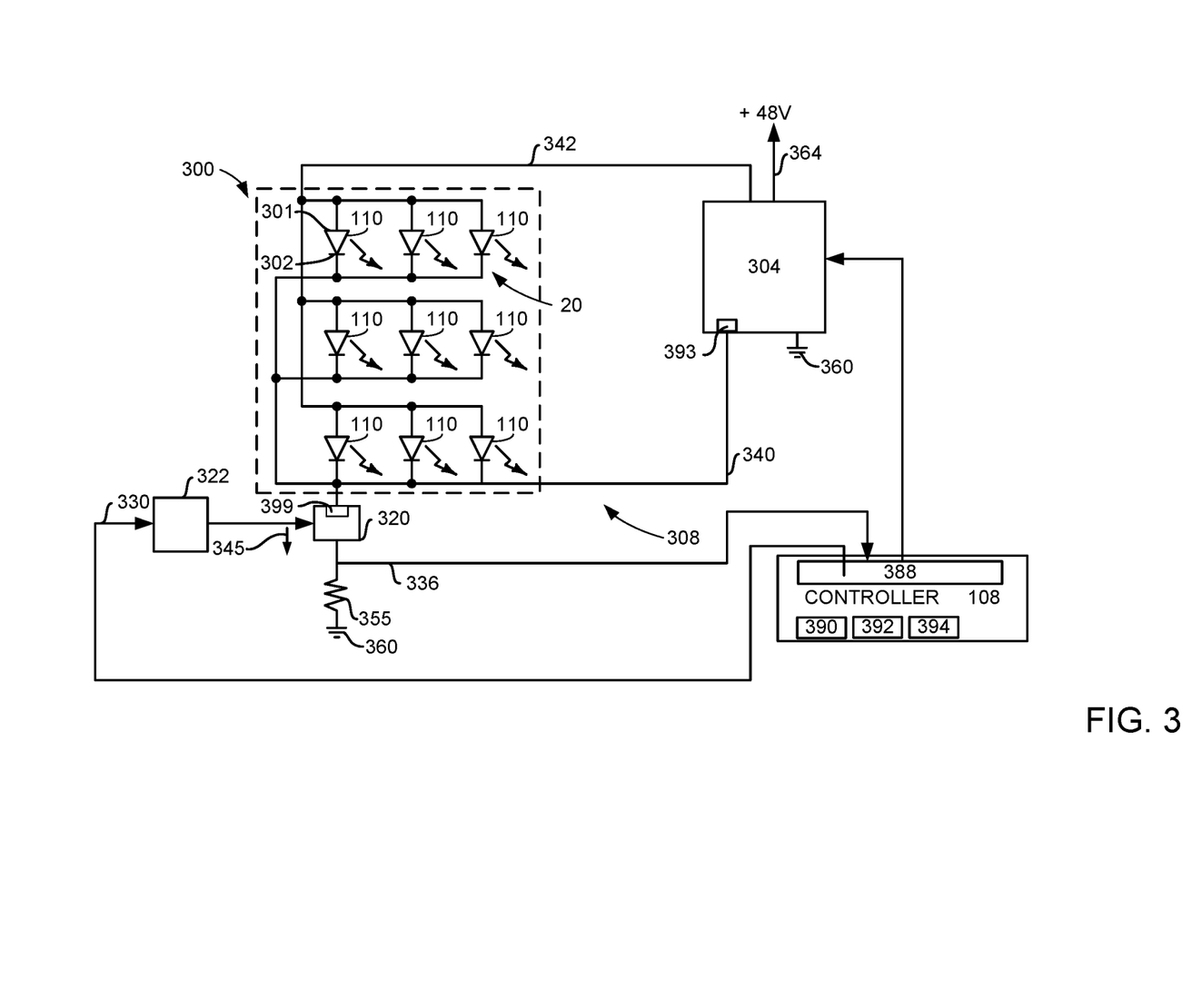
FIG. 3 depicts an example lighting system circuit that supplies varying amounts of a drive current to the lighting system of FIG. 1.

Referring to FIG. 3, a schematic of a lighting system circuit that may supply varying amounts of current to the lamp system of FIG. 1 is shown. In one example, the method of FIG. 2 is implemented via the circuit of FIG. 3, such as when potentiometer adjustments are made.

Lighting system 300 includes one or more light emitting devices 110. In this example, light emitting devices 110 are light emitting diodes (LEDs). Each LED 110 includes an anode 301 and a cathode 302. Switching power source 102 shown in FIG. 1 supplies 48V DC power to voltage regulator 304 via path or conductor 364. Voltage regulator 304 supplies DC power to the anodes 301 of LEDs 110 via conductor or path 342. Voltage regulator 304 is also electrically coupled to cathodes 302 of LEDs 110 via conductor or path 340. Voltage regulator 304 is shown referenced to ground 360 and may be a buck regulator in one example. Controller 108 is shown in electrical communication with voltage regulator 304. In other examples, discrete input generating devices (e.g., switches) may replace controller 108, if desired. Controller 108 includes central processing unit 390 for executing instructions. Controller 108 also includes inputs and outputs (I/O) 388 for operating voltage regulator 304 and other devices. Non-transitory executable instructions may be stored in read only memory 392 while variables may be stored in random access memory 394. Voltage regulator 304 supplies an adjustable voltage to LEDs 110.

Variable resistor 320 in the form of a field-effect transistor (FET) receives an intensity signal voltage from controller 108 or via another input device. While the present example describes the variable resistor as an FET, one must note that the circuit may employ other forms of variable resistors.

In this example, at least one element of array 20 includes solid-state light-emitting elements such as light-emitting diodes (LEDs) or laser diodes produce light. The elements may be configured as a single array on a substrate, multiple arrays on a substrate, several arrays either single or multiple on several substrates connected together, etc. In one example, the array of light-emitting elements may consist of a Semiconductor Light Matrix™ (SLM) manufactured by Phoseon Technology, Inc.

The circuit shown in FIG. 3 is a closed loop current control circuit 308. In closed loop circuit 308, the variable resistor 320 receives an intensity voltage control signal via conductor or path 330 through the drive circuit 322. The variable resistor 320 receives its drive signal from the driver 322. Voltage between variable resistor 320 and array 20 is controlled to a desired voltage as determined by voltage regulator 304. The desired voltage value may be supplied by controller 108 or another device, and voltage regulator 304 controls voltage signal 342 to a level that provides the desired voltage in a current path between array 20 and variable resistor 320. Variable resistor 320 controls current flow from array 20 to current sense resistor 355 in the direction of arrow 345. The desired voltage may also be adjusted responsive to the type of lighting device, type of work piece, curing parameters or decontamination cycle parameters, and various other operating conditions. An electrical current signal may be fed back along conductor or path 336 to controller 108 or another device that adjusts the intensity voltage control signal provided. In particular, if the electrical current signal is different from a desired electrical current, the intensity voltage control signal passed via conductor 330 is increased or decreased to adjust electrical current through array 20. A feedback current signal indicative of electrical current flow through array 20 is directed via conductor 336 as a voltage level that changes as electrical current flowing through current sense resistor 355 changes.

In one example where the voltage between variable resistor 320 and array 20 is adjusted to a constant voltage, current flow through array 20 and variable resistor 320 is adjusted via adjusting the resistance of variable resistor 320. Thus, a voltage signal carried along conductor 340 from the variable resistor 320 does not go to the array 20 in this example. Instead, the voltage feedback between array 20 and variable resistor 320 follows conductor 340 and goes to a voltage regulator 304. The voltage regulator 304 then outputs a voltage signal 342 to the array 20. Consequently, voltage regulator 304 adjusts its output voltage in response to a voltage downstream of array 20, and current flow through array 20 is adjusted via variable resistor 320. Controller 108 may include instructions to adjust a resistance value of variable resistor 320 in response to array current fed back as a voltage via conductor 336. Conductor 340 allows electrical communication between the cathodes 302 of LEDs 110, input 399 (e.g., a drain of an N-channel MOSFET) of variable resistor 320, and voltage feedback input 393 of voltage regulator 304. Thus, the cathodes 302 of LEDs 110 an input side 399 of variable resistor 320 and voltage feedback input 399 are at the same voltage potential.

The variable resistor may take the form of an FET, a bipolar transistor, a digital potentiometer or any electrically controllable, current limiting device. The drive circuit may take different forms depending upon the variable resistor used. The closed loop system operates such that an output voltage regulator 304 remains about 0.5 V above a voltage to operate array 20. The regulator output voltage adjusts voltage applied to array 20 and the variable resistor controls current flow through array 20 to a desired level. The present circuit may increase lighting system efficiency and reduce heat generated by the lighting system as compared to other approaches. In the example of FIG. 3, the variable resistor 320 typically produces a voltage drop in the range of 0.6V. However, the voltage drop at variable resistor 320 may be less or greater than 0.6V depending on the variable resistor's design.

Thus, the circuit shown in FIG. 3 provides voltage feedback to a voltage regulator to control the voltage drop across array 20. For example, since operation of array 20 results in a voltage drop across array 20, voltage output by voltage regulator 304 is the desired voltage between array 20 and variable resistor 320 plus the voltage drop across array 20. If the resistance of variable resistor 320 is increased to decrease current flow through array 20, the voltage regulator output is adjusted (e.g., decreased) to maintain the desired voltage between array 20 and variable resistor 20. On the other hand, if the resistance of variable resistor 320 is decreased to increase current flow through array 20, the voltage regulator output is adjusted (e.g., increased) to maintain the desired voltage between array 20 and variable resistor 20. In this way, the voltage across array 20 and current through array 20 may be simultaneously adjusted to provide a desired light intensity output from array 20. In this example, current flow through array 20 is adjusted via a device (e.g., variable resistor 220) located or positioned downstream of array 20 (e.g., in the direction of current flow) and upstream of a ground reference 360.

In this way, a data collection and monitoring method allows for improvements in calibration and equalization for a solid-state lighting device. The solid-state UVC lamp can now be configured to programmatically calibrate a multi-channel SLM UV lamp across a wide range of operational conditions, and across the product's life cycle, without exposing operators to UV radiation, and without requiring technician access or intervention to the product once in the field.

It will be appreciated that while the description pertains to a UVC lamp having a solid-state SLM light source, such as a UVC lamp used for inactivating RNAse, bacteria, and viruses, in other examples, a similar approach for calibration and equalization may be applied in machines where light is used for curing.

Turning to FIG. 4, an example timeline 400 is shown for calibrating a solid-state UVC lamp, such as according to the example method 200 of FIG. 2. Timeline 400 depicts a drive current provided from a potentiometer of an electrical circuit to a first channel of the SLM matrix at plot 402 and a second channel of the SLM matrix at plot 403. Lamp temperature is shown at plot 404. The irradiance output by the first SLM channel of the lighting system is shown at plot 406 in relation to a target irradiance and upper and lower thresholds, which define an acceptable range of irradiance. The irradiance output by the second SLM channel of the lighting system is shown at plot 408 in relation to the target irradiance and upper and lower thresholds, which define the acceptable range of irradiance. The upper and lower thresholds may in one example be +/−2.5% of the target. A calibration flag status is shown at plot 410. All plots are shown over time along the x-axis. Plots 406 and 408 are shown as segments, as the irradiance output by the first and second channels, respectively, may only be measured during specified time periods in the example of timeline 400. Furthermore, the drive currents of plots 402 and 403 are shown with respect to a maximum current (I_max), above which the drive current may not be further increased.

Prior to time t1, the lamp is turned off and no power (e.g., current) is being supplied to the lamp. At t1, a calibration time is confirmed, and power to the lamp is resumed. Specifically, a drive current is provided to the first channel (plot 402) and the second channel (plot 403). The drive current supplied to both of the first channel and the second channel is maintained relatively constant prior to t2 and is the same for each of the first channel and the second channel. For example, a controller performing the calibration may set a default starting potentiometer value on both channels corresponding to a median drive current from observed SLM matrix characteristics.

At time t2, the lamp reaches a thermal equilibrium where the temperature is largely constant. In response to the lamp reaching thermal equilibrium, between time t2 and time t3, the irradiance output of the first channel (plot 406) is measured by a first photosensor that corresponds to the first channel, and the irradiance output of the second channel (plot 408) is measured by a second photosensor that corresponds to the second channel. For example, due to the power being provided, an irradiance is output from the first and second channels, which is received at the corresponding photosensor. Although a continuous measurement is shown, it should be understood that a plurality of discreet irradiance measurements may be taken between time t2 and time t3 (e.g., one measurement taken every 200 ms for five measurements). Between time t2 and time t3, the irradiance of the first channel (plot 406) is below the upper threshold and above the lower threshold, and therefore within the acceptable range of the target, but the irradiance of the second channel (plot 408) is above the upper threshold, and therefore outside of the acceptable range of the target. In response to the irradiance of the second channel (plot 408) being above the upper threshold, at time t3, the drive current of the second channel (plot 403) is decreased, while the drive current of the first channel (plot 402) is maintained. Because the drive current of the second channel is decreased, the lamp temperature (plot 404) decreases.

At time t4, the lamp temperature (plot 404) is again determined to be in equilibrium (e.g., at a lower equilibrium temperature than that reached at time t2). In response to the lamp reaching thermal equilibrium, between time t4 and time t5, the irradiance output of the first channel (plot 406) is again measured by the first photosensor, and the irradiance output of the second channel (plot 408) is again measured by the second photosensor. Because the irradiance output of each channel of the SLM is temperature-dependent, even though the drive current of the first channel (plot 402) was maintained, the lower lamp temperature (plot 404) results in higher irradiance output by the first channel (plot 406). Between time t4 and time t5, the irradiance of the second channel (plot 408) is now between the upper threshold and the lower threshold and within the acceptable range of the target, but the irradiance of the first channel (plot 406) is now higher than the upper threshold. In response to the irradiance of the first channel (plot 406) being above the upper threshold, at time t5, the drive current of the first channel (plot 402) is decreased, while the drive current of the second channel (plot 403) is maintained. Because the drive current of the first channel is decreased, the lamp temperature (plot 404) further decreases.

At time t6, the lamp temperature (plot 404) is again determined to be in equilibrium (e.g., at a lower equilibrium temperature than that reached at time t4). In response to the lamp reaching thermal equilibrium, between time t6 and time t7, the irradiance output of the first channel (plot 406) is again measured by the first photosensor, and the irradiance output of the second channel (plot 408) is again measured by the second photosensor. Due to the decreased lamp temperature, the irradiance output by the second channel (plot 408) is higher even though the drive current to the second channel (plot 403) was maintained. However, the irradiance output by the second channel (plot 408) remains between the upper threshold and the lower threshold and within the acceptable range of the target. Furthermore, due to the decreased drive current to the first channel (plot 402), the irradiance of the first channel (plot 406) is within the acceptable range of the target. In response to the irradiance of both the first channel and the the second channel being within the acceptable range of the target, at time t7, a flag is set to indicate that calibration has been completed. Furthermore, the lamp may be turned off, with the drive current to the first and second channels (plots 402 and 403, respectively) reduced to zero.

Next, FIG. 5 shows a perspective view 500 of the array of light-emitting semiconductor devices 120 introduced in FIG. 1 positioned vertically above (e.g., with respect to the z-axis of reference axes 599) a lens array 528 covering a microplate 526, such as at a vertical distance 506. Components of FIG. 5 previously introduced in FIG. 1 are numbered the same and may not be reintroduced. The lens array 526 may be included in the coupling optics 130 of FIG. 1, for example. The microplate 526 may be positioned on a surface of the workpiece 126 shown in FIG. 1, such as for decontamination. The microplate 526 includes a plurality of wells 508, and the lens array 528 includes a plurality of lenses 530, with one lens 530 for each well 508. Each of the plurality of lenses 530 is positioned over and aligned with one of the plurality of wells 508. The lens array 528 may include Fresnel lenses, half-ball lenses, standard lenses, etc., and may be transparent to UV light.

The array of light-emitting semiconductor devices 120 is shown having two channels and is positioned at a left-most (e.g., smallest y-value with respect to the reference axes 599) position of the microplate 526 in the perspective view 500. In order to decontaminate the microplate 526, the array of light-emitting semiconductor devices 120 is first calibrated, such as according to the example method of FIG. 2 and as illustrated in the example timeline of FIG. 4, to ensure that the two channels achieve the same output intensity. Although two channels are shown, it should be understand that more or fewer channels may be included. In particular, because a width 512 of the microplate 526 is greater than a width 516 of the array of light-emitting semiconductor devices 120, the array of light-emitting semiconductor devices 120 may be linearly translated in the y-direction across the width of the microplate 526 (e.g., in a space above the microplate 526) in a scanning direction 504 until reaching a right-most position of the microplate 526. The array of light-emitting semiconductor devices 120 may be linearly moved by the motorized linear stage 155 shown in FIG. 1, for example. Furthermore, a length 514 of the array of light-emitting semiconductor devices 120 (e.g., in the x-direction) may be longer than a length 510 of the microplate 526, at least in some examples. Therefore, the array of light-emitting semiconductor devices 120 does not span the entire width 512 of the microplate 526, but does span the entire length 510 of the microplate 526.

As the array of light-emitting semiconductor devices 120 is translated in the scanning direction 504, the vertical distance 506 between the lens array 528 and the array of light-emitting semiconductor devices 120 is maintained such that the array of light-emitting semiconductor devices 120 does not touch the lens array 528. During the scanning, the plurality of semiconductor devices 119 are activated to emit the radiant output 124, which is directed vertically down to the microplate 526 via the lens array 528. The lens array 528 may focus the radiant output 124 across different, targeted surfaces of the microplate 526 as the array of light-emitting semiconductor devices 120 is linearly translated in order to completely decontaminate the microplate 526. Furthermore, due to the calibration of the two channels, the irradiation is relatively uniform for uniform decontamination.

It will be appreciated that while the system and methods described herein are described with reference to UV light, the systems and methods may be similarly applied to balance LED arrays of any wavelength. Further, the balancing may be extended to uses in addition to decontamination. Other uses may be include, for example, curing of inks, curing of medical devices, and manufacturing applications.

One example method, comprises: during a first stabilized temperature condition of a semiconductor light matrix (SLM), adjusting a drive current of the SLM based on an irradiance output by light-emitting diodes of the SLM to achieve a target irradiance; and in response to reaching a second stabilized temperature condition, re-adjusting the drive current of the SLM based on the irradiance output by the light-emitting diodes to maintain the target irradiance. In the preceding example, additionally or optionally, the light-emitting diodes are configured to emit short-wavelength ultraviolet (UV) light, including UV-C and/or UV-B light. In any or all of the preceding examples, additionally or optionally, the irradiance output by the light-emitting diodes is measured by photosensors. In any or all of the preceding examples, additionally or optionally, the irradiance output by the light-emitting diodes is measured while the light-emitting diodes are centered over the photosensors. In any or all of the preceding examples, additionally or optionally, the method further comprises actuating a motorized linear stage to linearly move the SLM so that the light-emitting diodes of the SLM are centered over the photosensors. In any or all of the preceding examples, additionally or optionally, the adjusting the drive current of the SLM based on the irradiance output by the light-emitting diodes comprises: responsive to the irradiance output by the light-emitting diodes being above an upper threshold, decreasing the drive current; and responsive to the irradiance output by the light-emitting diodes being below a lower threshold, increasing the drive current. In any or all of the preceding examples, additionally or optionally, the upper threshold is 2.5% greater than the target irradiance, and the lower threshold is 2.5% less than the target irradiance. In any or all of the preceding examples, additionally or optionally, the decreasing the drive current is for light-emitting diodes of a first array of the SLM and wherein the increasing the drive current is for light-emitting diodes of a second, different array of the SLM. In any or all of the preceding examples, additionally or optionally, the method further comprises estimating diode operating temperature intermittently via a thermocouple coupled to the SLM; saving intermittently estimated diode temperature values in a circular buffer; and confirming the first or the second stabilized temperature condition based on a linear regression analysis of the intermittently estimated diode temperature values in the circular buffer. In any or all of the preceding examples, additionally or optionally, the matrix is not functionally operational between the first and second temperature equilibrium conditions.

Another example irradiation system comprises: a semiconductor light matrix (SLM) including a plurality of channels and configured to emit radiation downward, relative to a vertical direction, toward a workpiece; a motorized linear stage adapted to linearly move the SLM in an orthogonal direction, relative to the vertical direction; a temperature sensor coupled to the SLM; and a plurality of photosensors positioned below, with respect to the vertical direction, the SLM. In any or all of the preceding examples, additionally or optionally, the system further comprises a controller, that holds executable instructions stored in non-transitory memory that, when executed, cause the controller to actuate the motorized linear stage to linearly move the SLM so that the SLM is vertically aligned with the plurality of photosensors; and calibrate the plurality of channels of the SLM while the SLM is vertically aligned with the plurality of photosensors. In any or all of the preceding examples, additionally or optionally, the instructions that cause the controller to calibrate the plurality of channels of the SLM while the SLM is vertically aligned with the plurality of photosensors include further instructions that, when executed, cause the controller to measure the radiation emitted by the SLM via the photosensors in response to a temperature equilibrium condition measured by the temperature sensor; and adjust a drive current provided to the SLM based on the measured radiation. In any or all of the preceding examples, additionally or optionally, the temperature equilibrium condition is a first temperature equilibrium condition, and wherein the controller includes further instructions to measure the radiation emitted by the SLM via the photosensors in response to a second temperature equilibrium condition measured by the temperature sensor, and readjust the drive current provided to the SLM based on the measured radiation, wherein there is no functional operation of the matrix between the first and second temperature equilibrium conditions. In any or all of the preceding examples, additionally or optionally, calibrating the channels includes measuring, via the plurality of photosensors, an irradiance output by light-emitting diodes arranged in the channels.

Another example method comprises, during a stabilized temperature condition of an array of semiconductor light emitters, adjusting a drive current applied to the array based on an irradiance output by light-emitting sensors positioned to receive output of the array, the drive current adjusted to achieve a target irradiance. In any or all of the preceding examples, additionally or optionally, the semiconductor light emitters are arranged in a combined series and parallel electrical configuration to form the array. In any or all of the preceding examples, additionally or optionally, the emitters are ultraviolet (UV)-C emitters. In any or all of the preceding examples, additionally or optionally, one of the array and the light-emitting sensors are moveably mounted with respect to each other via an electric actuator, including an electric motor. In any or all of the preceding examples, additionally or optionally, the array is one of a plurality of arrays coupled in a semiconductor light matrix lamp, and wherein the drive current is adjusted for one or more additional arrays of the plurality of arrays at least twice before applying output emitted from the lamp for a decontamination function, the decontamination function including treating an organism with the output emitted from the lamp to be killed.

As will be appreciated by one of ordinary skill in the art, the methods described in FIG. 2 may represent one or more of any number of processing strategies such as event-driven, interrupt-driven, multi-tasking, multi-threading, and the like. As such, various steps or functions illustrated may be performed in the sequence illustrated, in parallel, or in some cases omitted. Likewise, the order of processing is not necessarily required to achieve the objects, features, and advantages described herein, but is provided for ease of illustration and description. Although not explicitly illustrated, one of ordinary skill in the art will recognize that one or more of the illustrated steps or functions may be repeatedly performed depending on the particular strategy being used.

This concludes the description. The reading of it by those skilled in the art would bring to mind many alterations and modifications without departing from the spirit and the scope of the description. For example, lighting sources producing different wavelengths of light may take advantage of the present description.

The invention claimed is:
1. A method, comprising:
adjusting a position of a solid-state lighting device via a motorized linear stage such that the solid-state lighting device is centered over photosensors;
during a first stabilized temperature condition of the solid-state lighting device, adjusting a drive current of the solid-state lighting device based on an irradiance output by light-emitting diodes of the solid-state lighting device to achieve a target irradiance; and
in response to reaching a second stabilized temperature condition, re-adjusting the drive current of the solid-state lighting device based on the irradiance output by the light-emitting diodes to maintain the target irradiance.

2. The method of claim 1, wherein the light-emitting diodes are configured to emit short-wavelength ultraviolet (UV) light, including UV-C and/or UV-B light.

3. The method of claim 1, wherein the irradiance output by the light-emitting diodes is measured by the photosensors.

4. The method of claim 3, wherein the irradiance output by the light-emitting diodes is measured while the light-emitting diodes are centered over the photosensors.

5. A method, comprising:
adjusting a position of a solid-state lighting device by actuating a motorized linear stage such that the solid-state lighting device is centered over photosensors;
during a first stabilized temperature condition of the solid-state lighting device, adjusting a drive current of the solid-state lighting device based on an irradiance output by light-emitting diodes of the solid-state lighting device to achieve a target irradiance; and
in response to reaching a second stabilized temperature condition, readjusting the drive current of the solid-state lighting device based on the irradiance output by the light-emitting diodes to maintain the target irradiance;
wherein actuating the motorized linear stage linearly moves the solid-state lighting device so that the light-emitting diodes of the solid-state lighting device are vertically aligned with the photosensors, and wherein the irradiance output by the light-emitting diodes is measured by the photosensors while the light-emitting diodes are centered over the photosensors.

6. The method of claim 5, wherein the adjusting the drive current of the solid-state lighting device based on the irradiance output by the light-emitting diodes comprises:
responsive to the irradiance output by the light-emitting diodes being above an upper threshold, decreasing the drive current; and
responsive to the irradiance output by the light-emitting diodes being below a lower threshold, increasing the drive current.

7. The method of claim 6, wherein the upper threshold is 2.5% greater than the target irradiance, and the lower threshold is 2.5% less than the target irradiance.

8. The method of claim 6, wherein the decreasing the drive current is for light-emitting diodes of a first array of the solid-state lighting device and wherein the increasing the drive current is for light-emitting diodes of a second, different array of the solid-state lighting device.

9. The method of claim 5, further comprising:
estimating diode operating temperature intermittently via a thermocouple coupled to the solid-state lighting device;
saving intermittently estimated diode temperature values in a circular buffer; and
confirming the first or the second stabilized temperature condition based on a linear regression analysis of the intermittently estimated diode temperature values in the circular buffer.

10. The method of claim 5, wherein the solid-state lighting device is not functionally operational between the first and second stabilized temperature conditions.

11. An irradiation system, comprising:
a solid-state lighting device including a plurality of channels and configured to emit radiation downward, relative to a vertical direction, toward a workpiece;
a motorized linear stage adapted to linearly move the solid-state lighting device in an orthogonal direction, relative to the vertical direction;
a temperature sensor coupled to the solid-state lighting device; and
a plurality of photosensors positioned below, with respect to the vertical direction, the solid-state lighting device.

12. The irradiation system of claim 11, further comprising a controller, that holds executable instructions stored in non-transitory memory that, when executed, cause the controller to:
actuate the motorized linear stage to linearly move the solid-state lighting device so that the solid-state lighting device is vertically aligned with the plurality of photosensors; and
calibrate the plurality of channels of the solid-state lighting device while the solid-state lighting device is vertically aligned with the plurality of photosensors.

13. The irradiation system of claim 12, wherein the instructions that cause the controller to calibrate the plurality of channels of the solid-state lighting device while the solid-state lighting device is vertically aligned with the plurality of photosensors include further instructions that, when executed, cause the controller to:
measure the radiation emitted by the solid-state lighting device via the photosensors in response to a temperature equilibrium condition measured by the temperature sensor; and
adjust a drive current provided to the solid-state lighting device based on the measured radiation.

14. The irradiation system of claim 13, wherein the temperature equilibrium condition is a first temperature equilibrium condition, and wherein the controller includes further instructions to measure the radiation emitted by the solid-state lighting device via the photosensors in response to a second temperature equilibrium condition measured by the temperature sensor, and readjust the drive current provided to the solid-state lighting device based on the measured radiation, wherein there is no functional operation of the solid-state lighting device between the first and second temperature equilibrium conditions.

15. The irradiation system of claim 12, wherein calibrating the channels includes measuring, via the plurality of photosensors, an irradiance output by light-emitting diodes arranged in the channels.

16. A method, comprising:
adjusting a position of an array of semiconductor light emitters by actuating a motorized linear stage such that the array is centered over photosensors positioned to receive output of the array; and
during a stabilized temperature condition of the array, adjusting a drive current applied to the array based on an irradiance output by the photosensors, the drive current adjusted to achieve a target irradiance, wherein a length of the array of semiconductor light emitters is configured to be longer than a length of a workpiece with the photosensors.

17. The method of claim 16, wherein the semiconductor light emitters are arranged in a combined series and parallel electrical configuration to form the array.

18. The method of claim 16, wherein the emitters are ultraviolet (UV)-C emitters.

19. The method of claim 16, wherein one of the array and the photosensors are moveably mounted with respect to each other via an electric actuator, including an electric motor.

20. The method of claim 16, wherein the array is one of a plurality of arrays coupled in a semiconductor light matrix lamp, and wherein the drive current is adjusted for one or more additional arrays of the plurality of arrays at least twice before applying output emitted from the lamp for a decontamination function of the workpiece, the decontamination function including treating an organism with the output emitted from the lamp to be killed.

* * * * *